United States Patent
Karapetyan

(10) Patent No.: US 7,293,991 B1
(45) Date of Patent: Nov. 13, 2007

(54) DENTAL IMPLANT WITH THE FIXTURE INTERMEDIATE SUPPORT

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 11/367,739

(22) Filed: Mar. 3, 2006

(51) Int. Cl.
*A61C 8/00* (2006.01)
(52) U.S. Cl. ...................................... 433/173
(58) Field of Classification Search ......... 433/172–176
See application file for complete search history.

(56) References Cited

U.S. PATENT DOCUMENTS

| | | | |
|---|---|---|---|
| 4,468,200 A * | 8/1984 | Munch | 433/174 |
| 4,547,157 A * | 10/1985 | Driskell | 433/173 |
| 4,746,293 A | 5/1988 | Lundgren et al. | |
| 4,756,689 A | 7/1988 | Lundgren et al. | |
| 4,863,383 A | 9/1989 | Grafelmann | |
| 5,015,186 A * | 5/1991 | Detsch | 433/173 |
| 5,205,746 A * | 4/1993 | Chanavaz | 433/174 |
| 5,810,592 A * | 9/1998 | Daftary | 433/173 |
| 5,961,328 A * | 10/1999 | Somborac et al. | 433/173 |
| H1984 H * | 8/2001 | Salama et al. | 433/173 |
| RE38,945 E * | 1/2006 | Fried et al. | 433/172 |
| 2006/0199152 A1* | 9/2006 | Hurson et al. | 433/173 |

* cited by examiner

*Primary Examiner*—Cris Rodriguez
*Assistant Examiner*—Sunil K. Singh

(57) ABSTRACT

An improved dental implant with the fixture intermediate support includes an upper portion including a head comprising a main aperture of a cylindrical shape with a fine female thread, a fixture intermediate support including a cylindrical extension with the male fine thread fitting the fine-threaded (female fine thread) main aperture, and a lower portion including a shank comprising a male thread and a transverse isosceles trapeziumic hole crossing the threaded shank along the lateral axis. Also, an improved dental implant with the fixture intermediate support includes a main projection conventionally (conditionally) separating lower portion and upper portion.

3 Claims, 3 Drawing Sheets

DENTAL IMPLANT WITH THE FIXTURE INTERMEDIATE SUPPORT

FIELD OF THE INVENTION

This invention relates to a dental tooth implants and, more particularly, to the universal tooth implant embedded in the bone of a dental patient's jaw.

BACKGROUND OF THE INVENTION

There are at present a number of different dental implants in use. Mostly the dental implants include a solid artificial tooth (implant) root portion which is placed into a custom bored hole in the jaw bone, and the outer portion directly coupled with a crown. A prosthetic coronal section is attached to the artificial root portion when healing and bone integration of the artificial root portion is complete, and a dental prosthetic appliance such as a crown, denture or bridge is attached to the coronal section.

When posts are to be anchored for a fixation of dental suprastructures, such as bridges or web-like stiffeners, implants are inserted or screwed into a pilot bore, which sometimes has been drilled into the jaw bone.

One of the dental implants is disclosed in the U.S. Pat. No. 4,863,383. The described implant includes a screw, which is formed with sharp-edged screw threads on a tapered shank. The shank is integral with a socket, on which the self-tapping screw threads are continued. In accordance with the invention the depth of the screw threads continuously decrease to zero in the direction from the tip of the shank to the outer end of the socket 4 so that the outside diameter of the rod-shaped implant remains constant from its top to the inner end of the screw threads. A zero depth of the screw threads is reached 2 to 3 mm below the butt joint. To facilitate the self-tapping operation, one or more indentations are formed in each convolution of the screw threads. For the same purpose the shank if formed in its tip portion with notches, each of which has a sharp edge which extends generally in the longitudinal direction of the shank and defines a surface that faces in the sense in which the implant is rotated as it is screwed into the bore. Those side faces of the screw threads which face the tip of the shank are at right angles to the axis of the shank and those side faces which face the socket include an obtuse angle with said axis. The post comprises a stem, which at its inner end carries male screw threads. The socket has a socket opening, which has a non-circular outer portion, which may be hexagonal as shown in the illustrated embodiment, and which is engageable by a mating socket key. The socket opening comprises at its inner end a blind circular bore, which is formed with female screw threads. The male screw threads of the stem of the post are screwed into the female screw threads. Those portions of the socket and of the post which abut at the joint have cylindrical outside peripheral surfaces which are equal in diameter and flush with each other. To permit the post to be secured in the socket, the stem of the post is formed with recesses for receiving adhesive paste or cement of the like, which will prevent a rotation of the post. For the reasons stated hereinbefore the female screw threads and the male screw threads of the stem may be left-handed. The socket has at its outer end a circular outside rim, which is adjoined by a threadless cylindrical outside peripheral surface having an axial width of 2 to 3 mm. The socket tapers from said cylindrical outside surface to the shank. The self-tapping screw threads terminate at said cylindrical outside surface.

This dental implant eliminate the necessity to drill a bore into the bone, but there is no universality of the outer portion for interchangeability between the currently available crowns and/or crown's systems. So, that once an implant has been mounted on one type of artificial root, any future replacements must use the same crown attachment system. Since the average lifetime of a crown is of the order of 7-10 years, at which time a patient may have moved or be seeing a different dentist, significant problems can arise when a crown replacement is needed. The dental practitioner must always have the same crown systems on hand, since patients may have been fitted with various different types of implants at different times, and will also need the appropriate set of tools for mounting the various systems. This problem is likely to become more acute as the number of individuals fitted with such implant systems increases.

Another problem with existing attachment systems is that of adjusting for undesirable placement angulation of the submerged artificial root. Since the prosthetic coronal section or post normally extends coaxially from the artificial root, and the prosthesis must be mounted on this post, undesirable angulation may make it difficult to align the prosthetic tooth or teeth with the natural tooth line. This is a particular problem with front teeth, since for cosmetic reasons it is desirable that a screw or the like securing a crown or artificial tooth to the post does not exit through a front face of the tooth. Some attempts for adjusting angulation are provided in various existing systems, for example providing the post or prosthetic coronal section with a bendable neck portion, but this results in a weakened area which is liable to break. In other systems fixed angled portions are provided on the post, but this allows one angular adjustment only and thus does not allow easy adjustment or a wide range of angulation adjustment.

Another problem with replacing front teeth with existing implant systems is that the post or prosthetic section securing the artificial tooth or teeth to the implant will often be visible between the base of the tooth and the gum, particularly as the gum recedes naturally with time. This results in an unattractive gap which can be seen when the wearer smiles.

One of the dental implant attachment system is shown in U.S. Pat. No. 5,015,186. According to this invention, a dental implant attachment system for mounting a dental prosthesis on an artificial root implant comprises a base member having a lower end sized to seat on the upper end of the root implant cylinder and an upper end having an outer diameter substantially equal to that of a tooth for mounting on the implant, and a prosthetic head having a lower end for mounting on the upper end of the base member and an upper end for securing to a dental prosthesis. A securing assembly is provided to secure the base member to the implant cylinder and the prosthetic head to the base member. The base members include members sized to seat on any existing artificial implant cylinder, and members having upper ends of diameter equivalent to a variety of average natural tooth sizes, for example in the range from 3.5 mm to 7.0 mm. The prosthetic heads have lower end cuff portions sized to seat on the upper end of each of the base members with no overlap, and each have an upwardly projecting post portion preferably of tapering conical shape. The prosthetic heads include post portions at angles between 0 and 30 degrees to the cuff portion, to allow for angulation adjustment. The prosthetic heads include a 0.5-2 mm wide butt joint which allows for a thickness of metal and ceramic to be placed between the post portion and the edge of the base portion. The securing devices such as screw fasteners is provided for securing the selected base member to the implant cylinder and for securing the selected prosthetic head to the base member. The upper end of the base member and lower end of each prosthetic head include interengageable indexing formations for securing the prosthetic head against rotation on the base member in any one of a series of fixed, indexed positions. The angled prosthetic heads can be rotated through 360 degrees relative to the base member to select the indexed position providing the best possible angulation before locking the head to the base member. In one arrangement the interengageable formations comprise corresponding male and female configurations each having flats around their outer diameter. The male and female configurations comprise hexagon or octagon nut and bore formations. With an octagonal locking formations, the prosthetic head is engaged in any one of eight possible different angular indexed orientations relative to the base member.

The interengageable formations will prevent rotation between any of the prosthetic heads and the base member to which they are attached, reducing the risk of loosening of the attachment structure as a result of dental forces, and also allow rotation of the angled heads into any one of a plurality of different possible fixed, indexed positions to adjust for the optimum orientation of the angled heads in the jaw. The fixed orientation of interengageable locking formation of the base member when mounted in the jaw establishes an indexing position for orientation of the finished prosthesis made in the laboratory. Thus the prosthesis can be precisely positioned on to the base member in the mouth. Also, the prosthetic head includes an annular member having a concave indent for seating a convex end element of the post portion. The post portion can be swiveled relative to the concave indent to adjust the angle of the prosthetic head post as desired. In order to mount any type of prosthesis on any artificial root implant cylinder, the base member having the appropriate lower and upper end dimensions is selected. This member is suitably mounted and secured to the implant cylinder. An impression head is then fastened to the base member, and impression is taken. The impression head is removed and may be replaced with a healing cap or with a temporary crown form. An analog of the base member is then fastened to the impression head and the analog and impression head are inserted into the impression. A cast is then made, into which the analog is set at the appropriate orientation. The impression head is removed, and the cast model of the patient's jaw with the embedded analog is used in a laboratory on a dental surveyor to orient an appropriate prosthetic head, either with a straight, angled or swiveling post section for increased adjustability. The selected prosthetic head is mounted on the base member analog at the optimum angular orientation. An appropriate wax pattern is crafted by those skilled in the art to exactly fit the prosthetic head. The prosthetic cast is then made from the wax pattern, and the parts are disassembled. The dentist can then reassemble the parts, mounting the prosthetic head on the base member in the patient's jaw and then cementing or otherwise attaching the prosthesis to the prosthetic head. The indexing locking formations between the prosthetic head and base member allows indexing between clinical and laboratory work and also allows for correction of undesired placement angulation of the submerged implant cylinder by choice of suitable angled prosthetic heads. They also make the attachment structure into a single fixed unit since the separate parts cannot rotate relative to one another once they are secured together.

This device is complex, has tall outer portion and does not provide the universality of the lower portion (root portion) for interchangeability between the currently available crowns and/or crown's systems.

Some other connecting device are known in the art, for example, the devices described in U.S. Pat. Nos. 4,746,293 and 4,756,689. Referring to the U.S. Pat. No. 4,746,293, the device includes the upper portion of a spacer, which is disposed on an anchorage unit implanted in jawbone tissue. The spacer is provided with a central, cylindrical spacer screw designed specifically for this purpose with an extended, exteriorly threaded pin. The spacer is provided with a collar consisting of two surfaces: an outer horizontal surface and an obliquely inclined surface located inside the surface. The connecting device in the form of an outer, sleeve-shaped patrix 6 is connected to the spacer. The outer circumferential surface of the patrix connects to the outer prosthesis portion by casting, and the patrix is so designed that it surrounds the central spacer screws. The base of the patrix connects to the collar-shaped portion of the spacer by the intermediary of a resilient member in the form of an O-ring of high-quality rubber. The spacer and the spacer screw are preferably made of titanium, while the patrix is suitably made of dental gold. The obliquely inclined surface of the collar-shaped portion of the spacer forms, together with an upper horizontal surface on a cuff of the spacer, two of the walls of an annular tunnel for the resilient member, namely the lower horizontal wall and the oblique lateral wall. The remaining walls of the annular tunnel viz. the medial, vertical wall and the upper horizontal wall are formed by the circumferential surface of the spacer screw, which in this case is of circular profile, and the planar, lower base surface of the patrix, respectively. The annular tunnel is formed by the above-mentioned surface is adapted to the resilient member in the form of an O-ring of rubber. In this case, the O-ring is dimensioned to permit a deflection of the order of magnitude of about 100-200 .mu.m. In eccentric or oblique loading, this corresponds to a maximum angular displacement of 1.degree.-2.degree.

The patrix surface is so disposed as to depress the O-ring and provide the contemplated elastic transmission of forces between the outer prosthesis portion and the spacer (the fixture). The play provided between the patrix surface and the spacer collar surface should exceed 200 mu.m in order to permit the planned elastic deflection of 100-200 mu.m. The elastic connection is anchored (locked) by an interiorly threaded special nut manufactured of, for example, gold. The nut is screwed onto the exteriorly threaded pin of the spacer screw such that its lower peripheral end surface meets a horizontal heel on the patrix. The nut is screwed on so far that light compression of the O-ring is attained. This light compression or pre-tensioning may be exactly determined in that the screw slot which is disposed in the top of the nut is turned so as to register with a groove in the upper patrix edge. By provision of further two such groove markings in the patrix edge to which the screw slot can be turned, both moderate and hard pre-tensioning of the connecting device may be mode, depending upon the deflection amplitude which is deemed to be most purposeful in each individual situation. The upper surface of the special nut may be covered with, for example, a gold washer once it has been locked by a droplet of acrylate. Acrylate is then applied over the gold washer in order to fill the aperture through which the nut was applied.

According to the mentioned U.S. Pat. No. 4,756,689, the device comprises the upper portion of a spacer which is disposed on a fixture (not shown) implanted in the jawbone tissue. The spacer is provided with a central, cylindrical spacer screw with a threaded bore for a locking screw. The spacer is provided with a collar which, in the extant systems, forms a substrate for the mounting cap (matrix) which, in turn, is united with that crown or bridge construction which is to be set in place. The locking screw is provided with a conical, downwardly tapering surface for fixedly locking the cap. Both the spacer and the locking screw. Also device comprises the cap-shaped matrix, for example of dental gold, titanium or plastic. Its base connects to the spacer in the same manner as does the cap in the extant system. The matrix is provided with an exterior thread arrangement (M4.times.0.5) for a ring nut. The matrix is further provided with an abutment or shelf adapted to the resilient member in the form of, for example, an O-ring of high-quality rubber for example EPDM (ethylene-propylene) rubber and, is dimensioned to permit a downward deflection of the order of magnitude of α=100-200 mu.m in this case. The matrix has a conical through-passage which communicates with the conical surface of the locking screw. The locking screw rigidly draws the cap-shaped matrix fast in place for fixedly locking the mounting cap. In eccentric oblique loading, this corresponds to a maximum angular displacement "α" of 1°-2°, which is considered as fully satisfactory in view of possible connection to natural teeth.

The connecting device further includes a sleeve-shaped patrix, for example of titanium, plastic or gold, fitted with a heel which depresses the O-ring, and a inner portion running at right angles to the heel and enclosing, together with the heel, the matrix abutment or shelf and the matrix wall, the O-ring in a round tunnel of rectangular cross-section. In the production of the crown or bridge construction, respectively, the patrix is cast or fixed by other means in the crown/bridge which, through this patrix, will be elastically anchored to the matrix—the locking screw—the spacer. The resilient anchorage is locked by means of the ring nut, also manufactured of, for example, gold. The ring nut is threaded down to a light pre-tensioning of the O-ring, marked by a groove in the upper edge of the nut which must then register with a corresponding groove marking in the upper edge of the matrix. By a further two such markings in the matrix edge, both moderate and hard pre-tensioning of the connecting device are permitted. The upper surface of the connecting device may be covered with, for example, a gold washer, once the nut and the locking screw have been locked by a droplet of acrylate. Acrylate is applied over the gold washer in order to fill the aperture in the crown/bridge construction through which the locking screw and the ring nut have been sited in place.

This device is complex and requires a high-quality rubber O-ring, precision metals (e.g. such as a gold) and the patrix has to be elastically anchored to the matrix-the locking screw-the spacer, that is extremely expensive.

The aim of the present invention is therefore to provide a dental implant which does not have the mentioned above various disadvantages.

Thus, there is a great need in the art for the improved not complex, not expensive and reliable universal dental implant embedded in the bone of a person's (a dental patient's) jaw with the connecting portion for the crowns.

OBJECT AND ADVANTAGES OF THE INVENTION

Accordingly, several objects and advantages of the present invention are to provide reliable not complex and not expensive universal dental implant.

It is another object of the invention to provide the universal dental implant with the short upper portion for crown connection to the upper portion by the intermediate connecting portion (fixture intermediate support).

It is yet another object of the invention to provide the universal possibility to use an osteo-integrated implant for rigid connection with the artificial tooth or for connection providing the artificial tooth removability (e.g.: a clamping device, etc. for installation of the dental "bridge").

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

Most known dental implants are of a solid body configuration and are not adjustable to the different patients tooth height. There are no known dental implants with the fixture intermediate support (with the fixture [crown/bridge] connecting portion) providing the universal possibility to use an osteo-integrated implant for rigid connection with the different size artificial tooth (crown, bridge, etc.) or for connection providing the artificial tooth removability/replacement.

Thus, there is a great need in the art for the improved not complex, not expensive and reliable universal dental implant embedded in the bone of a person's (a dental patient's) jaw with the attachable connecting portion (with the different size connecting portions) for the crowns.

An improved dental implant with the fixture intermediate support includes an upper portion including a head comprising a main aperture of a cylindrical shape with a fine female thread, a fixture intermediate support including a cylindrical extension with the male fine thread fitting the fine-threaded (female fine thread) main aperture, and a lower portion including a shank comprising a male thread and a transverse isosceles trapeziumic hole crossing the threaded shank along the lateral axis. Also, an improved dental implant with the fixture intermediate support includes a main projection conventionally (conditionally) separating lower portion and upper portion.

DESCRIPTION OF THE PREFERRED EMBODIMENTS

Herein the description of an improved dental implant will be done in statics (as if the components of the improved device are suspended in the space) with the description of their relative coupling to each other. The description of the functional operations of the improved dental implant will be done hereinafter.

Figure 1A:
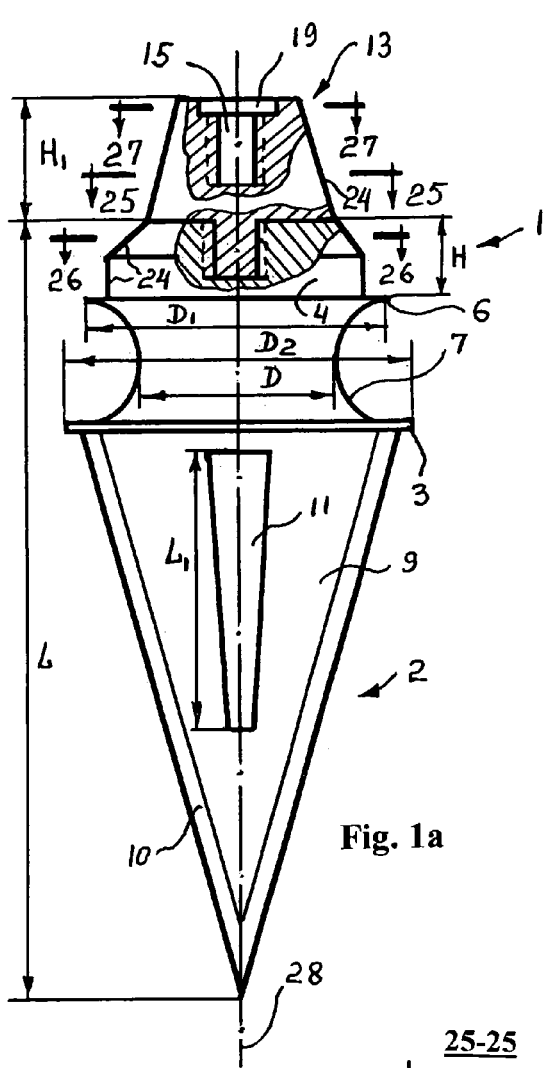
FIG. 1a is a simplified drawing of the improved dental implant with the fixture intermediate support.
Figure 2:
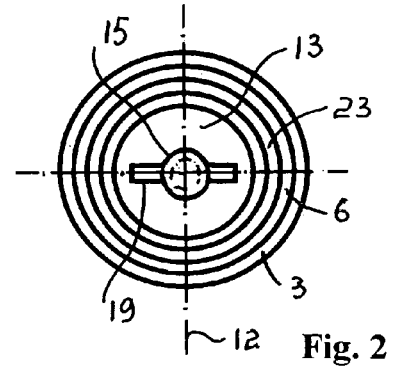
FIG. 2 is a simplified top view of the improved dental implant with the fixture intermediate support.
Figure 1B:
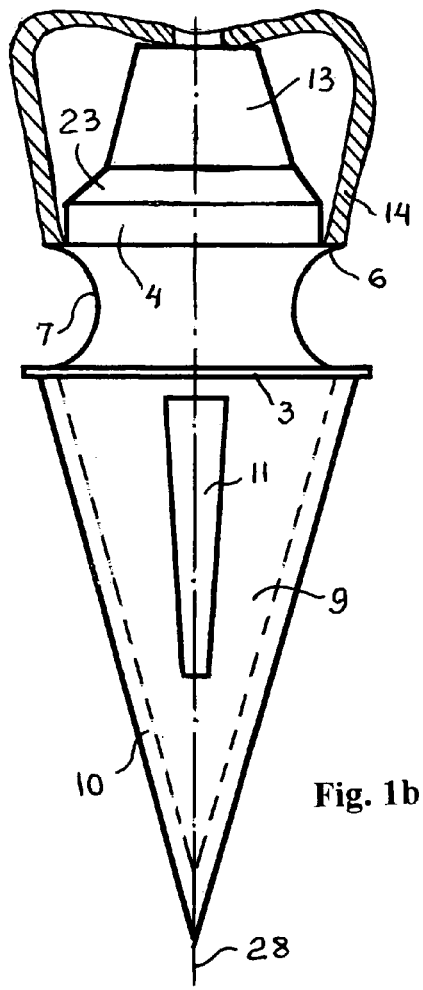
FIG. 1b is a simplified drawing of the improved dental implant with the fixture intermediate support and with the crown.
Figure 3:
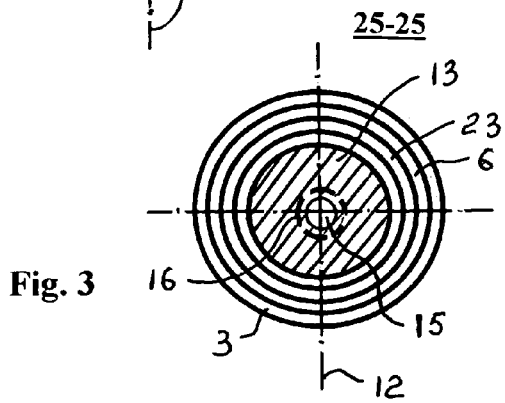
FIG. 3 is a cross-sectional view 25-25 of the improved dental implant with the fixture intermediate support.
Figure 5:
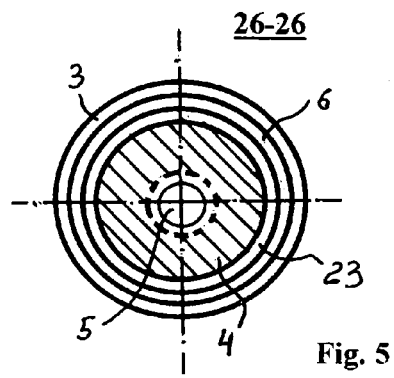
FIG. 5 is a cross-sectional view 26-26 of the improved dental implant.
Figure 6:
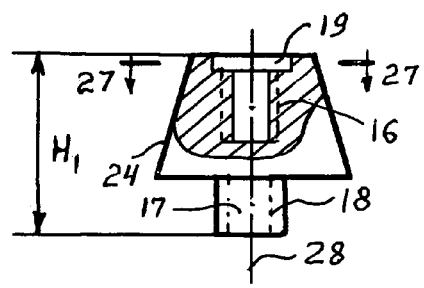
FIG. 6 is a simplified drawing of the first variant of the fixture intermediate support.
Figure 7:
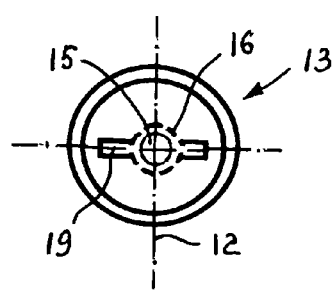
FIG. 7 is a simplified top view of the first variant of the fixture intermediate support.
Figure 8:
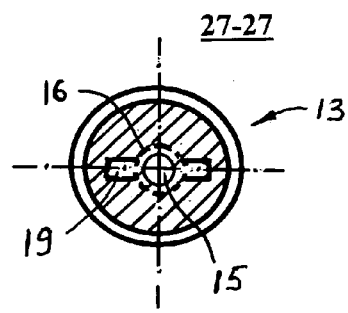
FIG. 8 is a cross-sectional view 27-27 of the first variant of the fixture intermediate support.
Figure 9:
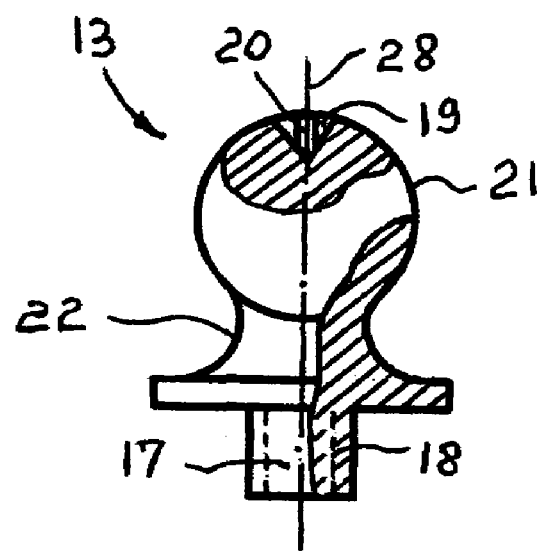
FIG. 9 is a simplified drawing of the second variant of the fixture intermediate support.
Figure 10:
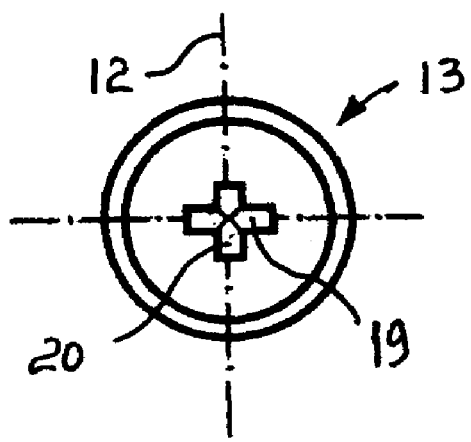
FIG. 10 is a simplified top view of the second variant of the fixture intermediate support.

An improved dental implant with the fixture intermediate support (fixture/crown connecting portion), referring to FIG. 1a, is an entire (solid) piece comprising the upper portion 1, the lower portion 2 and the main projection 3. The upper portion 1 includes a head 4 comprising a main aperture 5 of a cylindrical shape. The main aperture 5 is located longitudinally along the longitudinal (vertical) axis 28 of the dental implant with the fixture intermediate support (hereinafter the improved "dental implant with the fixture intermediate support" may be referred as "dental implant" or "implant", etc.) and includes an female fine thread 8. The head 4 can be of any regular geometrical shape/form and/or configuration, for example, of square, elliptical form, etc. or of any irregular form, for instance, squared-barrel form, etc. The preferred circular form of the head 4 of the improved implant includes the conic abutment 23 at its upper side. Also, the upper portion 1 includes the auxiliary projection 6 and the main groove 7. The diameter "D" of the main groove 7 is smaller than the diameter "$D_1$" of the auxiliary projection 6. As it is shown in FIG. 1a, the upper portion 1 is "conventionally separated" from the lower portion 2 by the main projection 3. The main projection 3 has preferably a cylindrical configuration, but the main projection 3 can also be of any reasonable configuration/form/shape, for example, of elliptical form, etc. The diameter "$D_2$" of the main projection 3 is bigger than the diameter "D" of the main groove 7, and bigger than the diameter "$D_1$" of the auxiliary projection 6 ($D_2$>$D_1$>D). Also, the upper portion 1 includes the connecting portion (a fixture intermediate support) 13 (see FIGS. 6-10) providing the coupling of the dental crown (bridge) 14 with the head 4, as it is shown in FIG. 1b. The coupling may be provided by the screw (not shown) fitting the auxiliary aperture 15 with the female thread 16. The connecting portion also includes a cylindrical extension 17 (see FIGS. 1a, 6, 9) with the male fine thread 18 fitting the fine-threaded (female fine thread 8) main aperture 5 (see FIGS. 1a, 4, 5). The connecting portion 13 comprises the slot 19 intended, for example, for the flat screwdriver (not shown) fitting at time of coupling with the head 4 as shown in FIG. 2, but the slot 19 with the additional slot 20 can form the "phillips" cross-slots for the possibility to use the "Phillips" screw drivers, as shown in FIGS. 9, 10, etc.

In FIGS. 1a, 2, 3, 6-8, the connecting portion 13 is for example shown of the truncated conic-shaped configuration. The connecting portion with the threaded (female thread 16) auxiliary aperture 15 can be used for the coupling (e.g. by the screw/not shown/) with the single crown or with the bridge (with the selected crown of the bridge). The connecting portion 13 is used for coupling of the dental implant with the detachable/removable bridge, as it is for instance shown in FIGS. 1a-3. The connecting portion 13 shown in FIGS. 9, 10 comprises a spherical-shaped upper part 21, an auxiliary groove 22 instead of the truncated conic-formed connecting portion 13 shown in FIGS. 1a, 2, 3, 6-8. Such configuration of the connecting portion 13, for example, allows the use of the clamping means (not shown) installed in the bridge's crown (not shown) and fitting the auxiliary groove 22. The connecting portion 13 and head 4 can include a rough outside surface or can include a texture 24 (see FIG. 1a) to secure unscrewing of connecting portion 13 and head 4.

The different people have different size of the teeth, i.e. smaller or bigger, therefore, the described of the above head 4 is a "short head" with the permanent predetermined height 'W' (H=const, wherein const—is "constant") in order to provide the possibility of the universality of the tooth implant and the possibility to adjust the different height crowns of the different dental patients to the short head 4 of the standard implant. It means, that the dentist can use (integrate in the patient jaw) the same kind of the implants for different patients attaching the connecting portions 13 between the head 4 of the implanted portion and different height crowns (i.e., a dentist chooses the connecting portion 13 of the appropriate height "$H_1$" ($H_1$=var, wherein var- is "variable") for the different height crowns 14).

Figure 4:
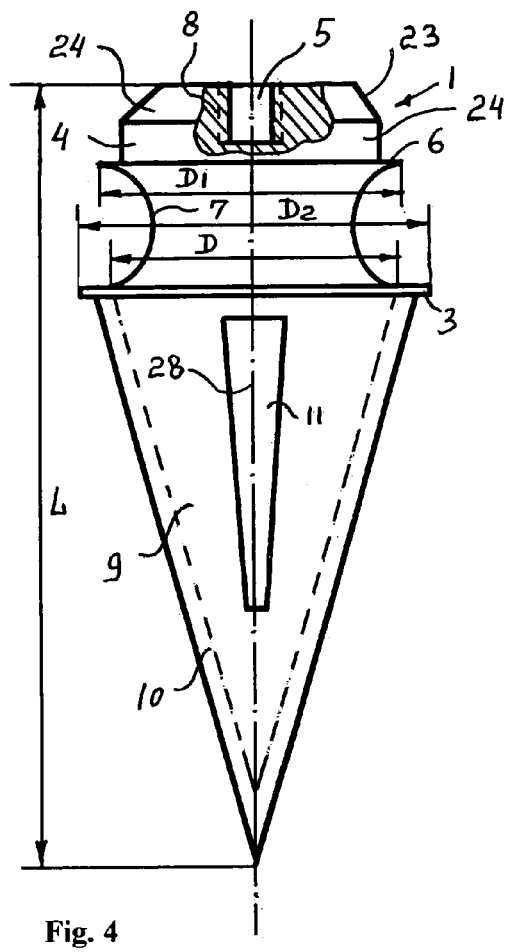
FIG. 4 is a simplified drawing of the improved dental implant.

The lower portion 2 comprises a shank 9 preferably of the conic configuration, as shown in FIGS. 1a, 4, but the shank 9 can be of any reasonable configuration, for instance, of a cylindric form, etc. The shank 9 includes an male thread 10 and the transverse isosceles trapeziumic hole (aperture) 11, crossing the threaded shank 9 along the lateral axis 12. The shank 9 can be threaded over the whole of its length, as it is for example shown in FIG. 1a.

The transverse isosceles trapeziumic hole 11 can cross the shank 9 along any transverse axis (e.g., lateral axis 12) around 360° along the lateral (horizontal) plane (not shown). The length "$L_1$" can approximately be preferably in the range of 4-8 mm, considering that the length ° "L" of the implant can vary in the range of 8-15 mm. The traverse isosceles trapeziumic hole 11 can be of any regular or irregular geometrical form, for example, of square, elliptical, rectangular form, etc. The transverse isosceles trapeziumic hole 11 provides a blood irrigation additionally to the blood passage via lower portion 2 circumference. As known, it thus contributes locally to maintaining the physiological equilibrium of the blood. It therefore counters the corresponding increase in acidity of the bone in this zone, and thus its becoming brittle. The blood passage in the space 14 thus returns the calcium content of the bone to normal. Such space also promotes the genesis of a bone "cortex" through the hole 11, which contributes to the blocking (or natural wedging) of the implant, and prevents the implant's pivoting in the bone socket after insertion. Additionally, as known from the dental practice it limits the progress of the dehiscence or resorption of the bone, as it is found in all the known implants after a period of the order of 5 to 7 years, by maintaining an osseous zone protected in the space 14. The transverse isosceles trapeziumic hole 11 is thus an element providing the stronger osseous destruction around the implant, and is an element for its biomechanical reinforcement.

The upper portion 1 and lower portion 2 can be not coaxial (can not be elongated along the longitudinal axis 28), and can be located under angle of approximately 5°-30° to each other (not shown).

All presented dimensions may vary depending on the reasonable unification aspect in the dental implant industry, and/or some other reasonable factors, e.g.: patient's natural teeth unique size, etc.

It should be understood that the above description discloses specific embodiments of the present invention and are for purposes of illustration only without any limitations.

There may be other modifications and changes obvious to those of ordinary skill in the art which fall within the scope of the present invention.

CONCLUSION, RAMIFICATION AND SCOPE

Accordingly the reader will see that, according to the invention, I have provided the improved dental implant with the fixture intermediate support. The improved dental implant has various possibilities, considering activities and applications of the implanted dental teeth.

While the above description contains many specificities, these should be not construed as limitations on the scope of the invention, but as exemplification of the presently-preferred embodiments thereof. Many other ramifications are possible within the teaching to the invention. For example, the improved dental implants with the fixture intermediate supports can easily be applicable for inserting in the front (nasal) mouth areas and in the pre-molar/molar mouth areas too.

Thus, the scope-of-the invention should be determined by the appended claims and their legal equivalents, and not by examples given.

THE DRAWING REFERENCE NUMERALS

1.—an upper portion;
2.—a lower portion;
3.—a main projection;
4.—a head;
5.—a main aperture;
6.—an auxiliary projection;
7.—a main groove;
8.—a female fine thread;
9.—a shank;
10.—a shank male thread;
11.—a transverse isosceles trapeziumic hole;
12.—a lateral axis;
13.—a fixture connecting portion (a fixture intermediate support);
14.—a fixture (a dental crown/bridge);
15.—an auxiliary aperture;
16.—a female thread;
17.—a cylindrical extension;
18.—a male fine thread;
19.—a slot;
20.—a cross-slot;
21.—a spherically-shaped upper part;
22.—an auxiliary groove;
23.—a conic abutment;
24.—a texture;
25-25 is a cross-sectional view;
26-26 is a cross-sectional view;
27-27 is a cross-sectional view;
28.—a longitudinal axis.

What is claimed is:

1. An improved dental implant with the fixture intermediate support includes
    a lower portion intended to be integrated to a jaw-bone, and wherein said lower portion comprises a shank of a conic configuration extended from a bottom side of a cylindrical main projection, and wherein said shank includes
        a transverse isosceles trapeziumic hole crossing said shank along a lateral axis;
        a male thread over the whole of the length of said shank;
    an upper portion extended from a top side of said main projection, and wherein said upper portion includes
        a main groove located between said main projection and an auxiliary projection; wherein said auxiliary projection having a diameter that is greater than a diameter of said main groove, and wherein said main projection having a diameter that is greater than said diameter of said auxiliary projection;
        a head extended from said auxiliary projection and comprising
            a cylindrical aperture located at the center of said head along a longitudinal axis;
            a female fine thread over the whole of the length of said cylindrical aperture;
    a fixture intermediate support coupled with said head and comprising
        an auxiliary aperture located at a top portion of said fixture intermediate support along said longitudinal axis, and wherein said auxiliary aperture includes a female thread over the whole of the length of said auxiliary aperture;
        a cylindrical extension located at the center of the bottom of said fixture intermediate support along said longitudinal axis, and wherein said cylindrical extension comprises a fine male thread over the whole of the length of said cylindrical extension that couples with said cylindrical aperture threaded by said female fine thread; wherein said head of said improved dental implant with fixture intermediate support further is of a cylindrical form with a conic abutment at an upper side of said head, and wherein said head comprises a textured surface.

2. The dental implant of claim 1, wherein said fixture intermediate support of said improved dental implant further is of a truncated conic form and comprises the fine threaded cylindrical extension or is of a spherically-shaped form with an auxiliary groove located in the bottom of the spherically-shaped fixture intermediate support and comprises said fine threaded cylindrical extension.

3. The dental implant of claim 2, wherein said fixture intermediate support of said improved dental implant further comprises a textured slant surface.

* * * * *